United States Patent
Palmer

(10) Patent No.: US 9,918,846 B2
(45) Date of Patent: Mar. 20, 2018

(54) METHOD TO IMPLANT A DISTAL RADIOULNAR JOINT DEVICE

(71) Applicant: Biomet Manufacturing, LLC, Warsaw, IN (US)

(72) Inventor: Andrew K. Palmer, Eastham, MA (US)

(73) Assignee: Biomet Manufacturing, LLC, Warsaw, IN (US)

( * ) Notice: Subject to any disclaimer, the term of this patent is extended or adjusted under 35 U.S.C. 154(b) by 36 days.

(21) Appl. No.: 14/468,835

(22) Filed: Aug. 26, 2014

(65) Prior Publication Data

US 2014/0364957 A1    Dec. 11, 2014

Related U.S. Application Data

(62) Division of application No. 13/713,063, filed on Dec. 13, 2012, now Pat. No. 8,840,674, which is a division
(Continued)

(51) Int. Cl.
*A61F 2/42* (2006.01)
*A61F 2/46* (2006.01)
(Continued)

(52) U.S. Cl.
CPC .......... *A61F 2/4261* (2013.01); *A61F 2/4606* (2013.01); *A61F 2/08* (2013.01); *A61F 2002/3055* (2013.01); *A61F 2002/30383* (2013.01); *A61F 2002/30387* (2013.01); *A61F 2002/30507* (2013.01); *A61F 2002/30579* (2013.01); *A61F 2002/30604* (2013.01); *A61F 2002/30772* (2013.01); *A61F 2002/30878* (2013.01); *A61F 2002/30884* (2013.01); *A61F 2002/4264* (2013.01); *A61F 2002/4269* (2013.01); *A61F 2220/0025* (2013.01)

(58) Field of Classification Search
CPC ... A61F 2/42; A61F 2/4261; A61F 2002/4269
See application file for complete search history.

(56) References Cited

U.S. PATENT DOCUMENTS

| 4,355,427 A | 10/1982 | Schneider |
| 5,658,340 A | 8/1997 | Muller et al. |

(Continued)

FOREIGN PATENT DOCUMENTS

| DE | 10237016 A1 * | 2/2004 | ........... A61F 2/4261 |
| WO | WO 2006048520 A1 * | 5/2006 | ........... A61F 2/4261 |

OTHER PUBLICATIONS

"U.S. Appl. No. 12/885,213, Examiner Interview Summary dated Sep. 25, 2012", 3 pgs.
(Continued)

*Primary Examiner* — Marcia Watkins
(74) *Attorney, Agent, or Firm* — Schwegman Lundberg & Woessner, P.A.

(57) ABSTRACT

A system and method of implanting a distal wrist implant relative to a host bone is presented. A distal radial component having a body including a first connection portion couplable to a stem is coupled to a second prosthetic coupled to a medial surface of the body. The second prosthetic replaces at least a portion of the sigmoid notch.

11 Claims, 12 Drawing Sheets

Related U.S. Application Data of application No. 12/885,213, filed on Sep. 17, 2010, now Pat. No. 8,366,784.

(60) Provisional application No. 61/243,381, filed on Sep. 17, 2009.

(51) Int. Cl.
*A61F 2/08* (2006.01)
*A61F 2/30* (2006.01)

(56) References Cited

U.S. PATENT DOCUMENTS

| | | | |
|---|---|---|---|
| 6,302,915 | B1 | 10/2001 | Cooney, III et al. |
| 7,288,115 | B2 * | 10/2007 | Hawkins ............... A61F 2/389 |
| | | | 623/20.14 |
| 7,875,082 | B2 | 1/2011 | Naidu |
| 8,366,784 | B2 | 2/2013 | Palmer |
| 8,840,674 | B2 | 9/2014 | Palmer |
| 2003/0014119 | A1 | 1/2003 | Capon et al. |
| 2004/0230312 | A1 * | 11/2004 | Hanson ............... A61F 2/4261 |
| | | | 623/21.12 |
| 2005/0203634 | A1 | 9/2005 | Bassik et al. |
| 2006/0161260 | A1 | 7/2006 | Thomas et al. |
| 2006/0229732 | A1 | 10/2006 | Bachelier |
| 2008/0027558 | A1 * | 1/2008 | Palmer ............... A61F 2/4261 |
| | | | 623/21.12 |
| 2008/0133023 | A1 | 6/2008 | Schlotterback et al. |
| 2008/0234829 | A1 | 9/2008 | Mutchler et al. |
| 2009/0254189 | A1 * | 10/2009 | Scheker ............... A61F 2/4261 |
| | | | 623/21.11 |

OTHER PUBLICATIONS

"U.S. Appl. No. 12/885,213, Final Office Action dated Jul. 23, 2012", 7 pgs.

"U.S. Appl. No. 12/885,213, Non Final Office Action dated Apr. 5, 2012", 10 pgs.

"U.S. Appl. No. 12/885,213, Notice of Allowance dated Oct. 3, 2012", 7 pgs.

"U.S. Appl. No. 12/885,213, Response filed Mar. 19, 2012 to Restriction Requirement dated Jan. 18, 2012", 7 pgs.

"U.S. Appl. No. 12/885,213, Response filed Jul. 2, 2012 to Non Final Office Action dated Apr. 5, 2012", 15 pgs.

"U.S. Appl. No. 12/885,213, Response filed Sep. 12, 2012 to Final Office Action dated Jul. 23, 2012", 10 pgs.

"U.S. Appl. No. 12/885,213, Restriction Requirement dated Jan. 18, 2012", 6 pgs.

"U.S. Appl. No. 13/713,063, 312 Amendment filed Jul. 7, 2014", 3 pgs.

"U.S. Appl. No. 13/713,063, Examiner Interview Summary dated Feb. 28, 2014", 3 pgs.

"U.S. Appl. No. 13/713,063, Non Final Office Action dated Nov. 22, 2013", 7 pgs.

"U.S. Appl. No. 13/713,063, Notice of Allowance dated Mar. 7, 2014", 8 pgs.

"U.S. Appl. No. 13/713,063, PTO Response to Rule 312 Communication dated Jul. 25, 2014", 2 pgs.

"U.S. Appl. No. 13/713,063, Response filed Feb. 24, 2014 to Non Final Office Action dated Nov. 22, 2013", 8 pgs.

"U.S. Appl. No. 13/713,063, Response filed Nov. 11, 2013 to Restriction Requirement dated Oct. 11, 2013", 3 pgs.

"U.S. Appl. No. 13/713,063, Restriction Requirement dated Oct. 11, 2013", 5 pgs.

\* cited by examiner

METHOD TO IMPLANT A DISTAL RADIOULNAR JOINT DEVICE

CROSS-REFERENCE TO RELATED APPLICATIONS

This application is a divisional of U.S. patent application Ser. No. 13/713,063 filed on Dec. 13, 2012, now U.S. Pat. No. 8,840,674, which is a divisional of U.S. patent application Ser. No. 12/885,213 filed on Sep. 17, 2010, now U.S. Pat. No. 8,366,784, which claims the benefit of U.S. Provisional Application No. 61/243,381, filed on Sep. 17, 2009. The entire disclosures of each of the above applications are incorporated herein by reference.

FIELD

The present teachings generally relate to prosthetic implants and more particularly to prosthetic wrist implants.

In a variety of wrist disorders, patients may experience discomfort, pain and difficulty in moving the wrist. Prior surgical treatment of this condition involved fusion to inhibit movement of the scaphoid and the lunate bones relative to the ulna to thereby alleviate pain in the patient's wrist. This procedure, however, leaves the patient without motion in their wrist and thereby severely restricts the use of their wrist. Prosthetic wrist implants have been developed to provide a pair of artificial bearing surfaces for the wrist. Several of the prior wrist implants have suffered from drawbacks including limited range of motion and excessive bone resection. Others still provide proper motion only when aligned in an extremely precise manner relative to the carpal bone complex. While various jigs and fixtures may be employed to aid in the locating and forming of a hole in the distal portion of the carpal bone complex for receiving a carpal implant, these devices typically do not completely eliminate the possibility of error in the alignment and forming of the hole.

Accordingly, there remains a need in the art for an improved prosthetic wrist implant that provides improved support and strength for the distal portion of the carpal bone complex and which has a bearing surface whose orientation is changeable after implantation to provide the implanted prosthetic wrist with a range of motion that mimics the range of motion of a natural wrist.

SUMMARY

According to the present teachings, a method of implanting a distal wrist implant relative to a host bone is presented. The distal radial component can have a body that includes a first connection portion couplable to a stem. A second prosthetic can be coupled to a medial surface of the body, the second prosthetic replacing at least a portion of the sigmoid notch. The distal radial component can be implanted relative to the host radius.

According to additional features, a flexible member can be located around at least some of the portions of the radial component. The flexible member can be located through apertures formed in the body. According to one example, soft tissue or soft tissue replacement can be passed through apertures formed in the body. In one example, the distal radial component and a sigmoid notch prosthetic together can include a slidably advanceable male extension portion formed on one of the distal radial component and the sigmoid portion into a female receiving portion formed on the other of the distal radial component and the sigmoid portion.

According to other features, a method of implanting a distal wrist implant relative to a host radius is presented. A prosthetic head is selected having a first coupling portion including opposing surfaces that define a slot. The head defines a passage that extends from an outer surface of the head to the slot. The head further defines a hole at a distal aspect thereof configured for receipt of one of a natural soft tissue replacement and an artificial soft tissue replacement. A stem may be selected having a second coupling portion extending upwardly from a surface of the stem. The second coupling portion can include first and second sides extending substantially parallel to each other. The second coupling portion can be advanced into the first coupling portion. A fastener can be advanced through a passage in the prosthetic head and a bore in the stem.

According to still other features, advancing the second coupling portion can include non-rotatably advancing the second coupling portion into the first coupling portion. An angled wall can be aligned on the second coupling portion with the hole in the head to accommodate receipt of one of the natural and artificial soft tissue replacement. The second coupling portion can have a third side, a fourth side opposite the third side, and a fifth side. The third, fourth and fifth sides can all extend between the first and second sides. The second coupling portion can further include the angled wall that non-orthogonally extends between the fourth side and the fifth side. Advancing the second coupling portion can comprise aligning the passage with the bore. Advancing the fastener can comprise threadably advancing the fastener into the bore.

A distal radial wrist implant operable to be implanted relative to a host radius according to the present teachings can include a distal radial component and a stem portion. The distal radial component can include a first body that has a medial articulation portion and a second body having a distal articulating surface. The second body can define a first connection portion. The first body portion is adapted to be implanted into the host radial and wherein the second body is operable to be slidably attached to the connection portion of the first body.

The present teachings provide in another aspect, a modular device system that will allow the device to be used for the following: ulnar head resurfacing, ulnar head partial resurfacing, and an ulnar head resurfacing with sigmoid notch resurfacing.

The present teachings provide in another aspect an ulnar head replacement device that utilizes a stem design, that may be varied to have multiple lengths, configurations (medial-lateral, distal-proximal, anterior-posterior) and outer diameters. Some additional unique components of the present teachings may include having a head that has a hole through which a tendon graft or other biomaterial may be passed when the joint is clinically unstable, thus allowing for a combined distal radioulnar joint replacement with ligamentous stabilization of the joint. A further aspect of the present teachings may be allowing for the head of the implant to be slipped onto the shaft from the side and then fixed with a mechanical locking mechanism (e.g., a screw) in contrast to the typical commercially available end-on design used with most implants.

The present teachings provide in yet another aspect a total distal radioulnar joint device that includes an ulnar head, a stem and a corresponding sigmoid notch replacement implant that has a portal for ligamentous reconstruction.

The present teachings provide further an ulnar head arthroplasty device that is used in conjunction with a commercially available total wrist implant in which the radial component of the total wrist implant has an integral articulation for the ulnar head. Essentially, the sigmoid notch of the radius has been replaced or resurfaced.

The present teachings provide in another aspect, a surgical instrumentation system that provides for site preparation, reproducible alignment and securement of the device following implantation and the accurate positioning of the various implantable devices to facilitate range of motion and appropriate joint laxity post-implantation.

The present teachings provide in yet another aspect, a surgical method for implanting the distal radioulnar joint device.

Further areas of applicability of the present teachings will become apparent from the detailed description provided hereinafter. It should be understood that the detailed description and various examples, while indicating the various embodiments of the teachings, are intended for purposes of illustration only and are not intended to limit the scope of the teachings or the claims.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

Figure 1:
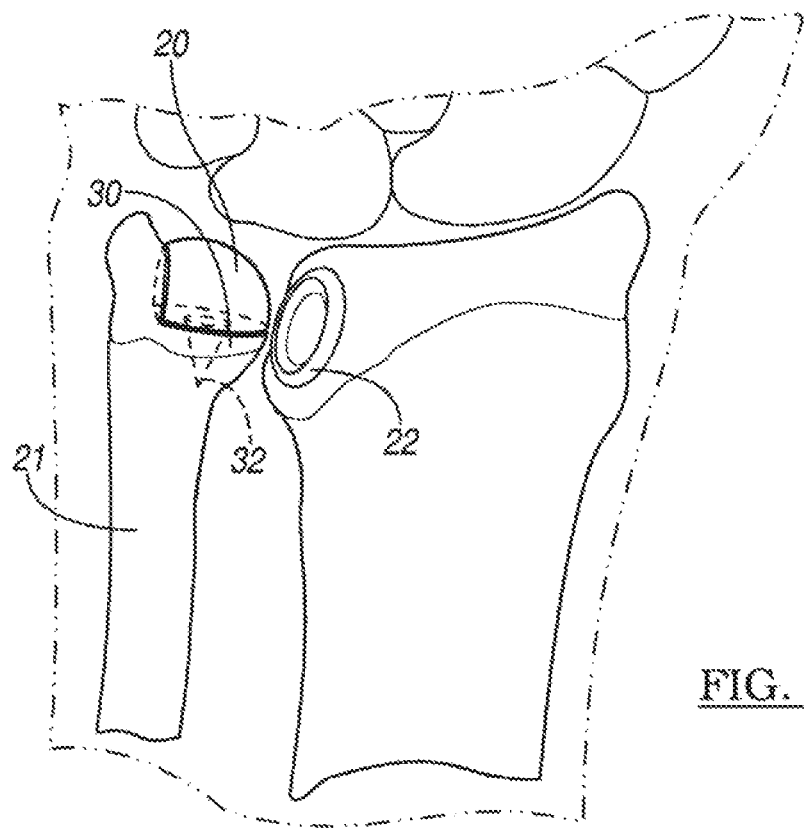
FIG. 1 represents a perspective view of a prosthetic system according to the present teachings.

FIG. 1 shows the distal end of the radius and ulna with a prosthetic according to the present teachings. As seen, the ulnar resurfacing implant 20 is used to resurface at least a portion of the articulating surface of the distal end of the ulna 21. Also shown in FIG. 1 is a prosthetic assembly 22 which functions as a resurfacing device for the sigmoid notch of the radius. With the modular platform technology, the surgeon could implant either the ulna resurfacing implant 20 alone, the sigmoid notch resurfacing implant 21 alone or both, in combination.

It is envisioned the ulna replacement implant 20 can replace only a portion of the articulating surface 30. Further, the implant 20 can be either monolithic or modular. The resurfacing the implant 20 can have affixation stem 32.

Figure 2:
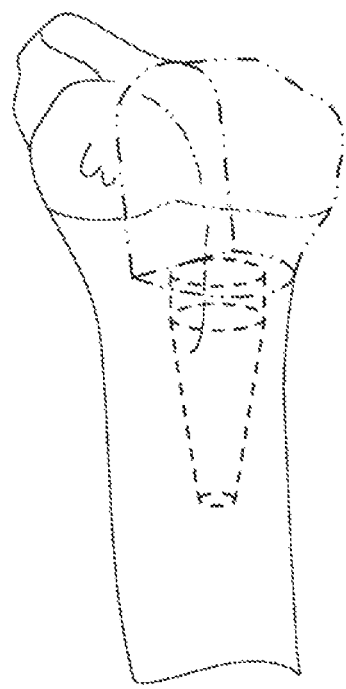
FIG. 2 represents a perspective view of a resected radius.

FIG. 2 represents a perspective view of the resection of the ulna. Shown are portions of the ulna to be resected during an implantation procedure. As described below in more detail, resection of the ulna can occur using a saw, rasp, or drill.

Figure 3A:
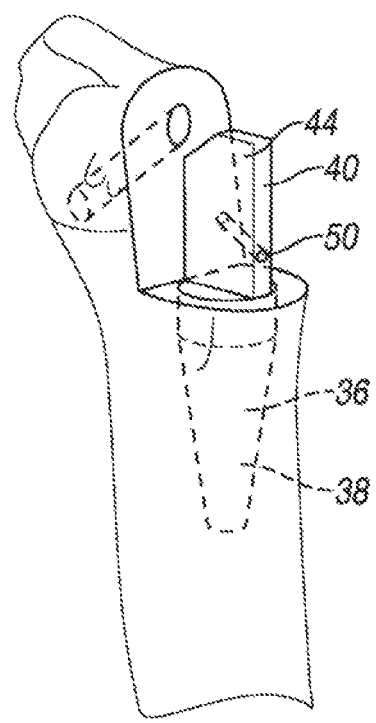
FIGS. 3A and 3B represent the assembly of the prosthetic according to the present teachings.
Figure 3B:
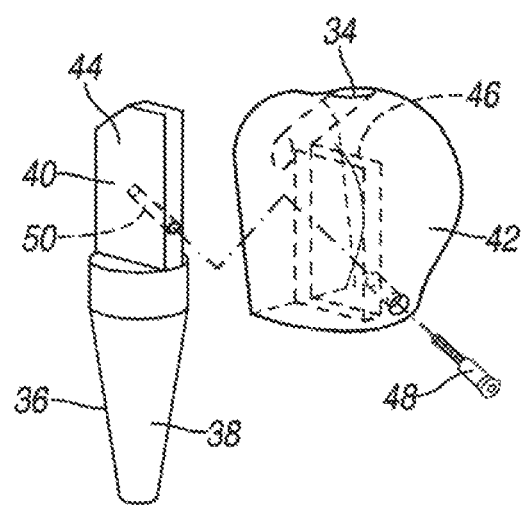

FIGS. 3A and 3B depict a modular replacement head 42 to replicate the size and shape of the natural ulnar head and fixation stem according to the present teachings. The replacement head 42 defines a hole 34 its distal aspect so as to accommodate securement of graft material or artificial ligament structures 35 to reestablish joint stability post-operatively. The hole 34 can be aligned with a corresponding hole 31 within the resected ulna.

As shown in FIG. 3A, the stem 36 has a first portion 38 which is used to couple the stem 36 to a resected bone. A second portion 40 is used to couple the prosthetic head 42 to the stem 36. The second portion 40 can be formed of a cylindrical or general planar coupling surface 44. The generally planar coupling surface 44 is configured to be disposed within slot 46 defined within the prosthetic head. After coupling the head 42 to the stem 36, a coupling fastener 48 is coupled to a threaded aperture 50 defined within the second portion of the stem.

Figure 4A:
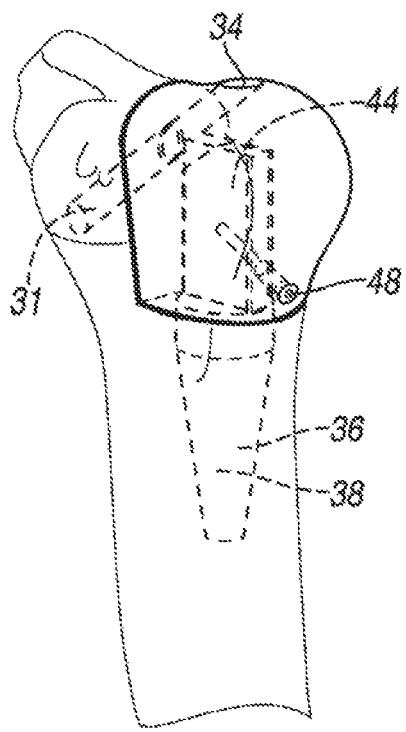
FIGS. 4A-4C represent perspective, cross-sectional, and top views of the prosthetic shown in FIG. 1.
Figure 4B:
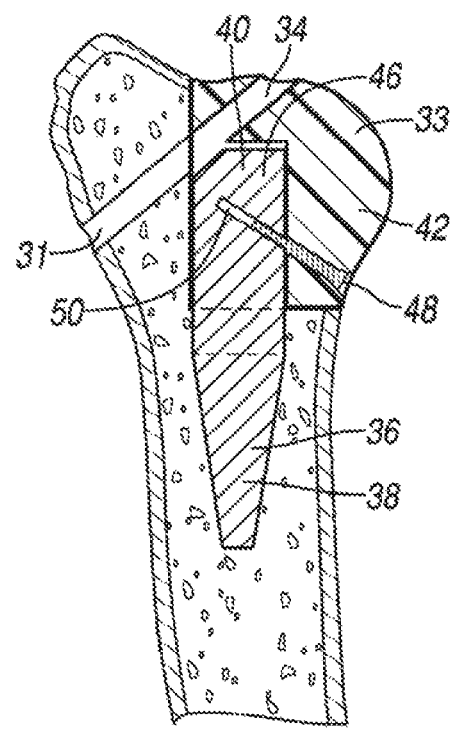
Figure 4C:
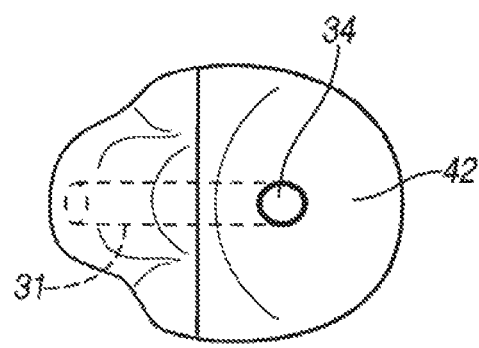

FIGS. 4A-4C represent perspective sectional and top views of the head coupled to the stem. As best shown in FIG. 4B, both the head and resected bone define a co-aligned through passage. The through passage is configured to accept a natural or artificial soft tissue replacement, suture or coupling wire.

Further disclosed are the methods for coupling the replacement head onto the implanted stem, wherein for example, the replacement head would slide onto the implanted stem from the side and utilize a multitude of possible locking mechanisms for securement. One example may be the shown securement screw that would engage the head from an inferior direction. Optionally, a coupling taper can be used.

Figure 5:
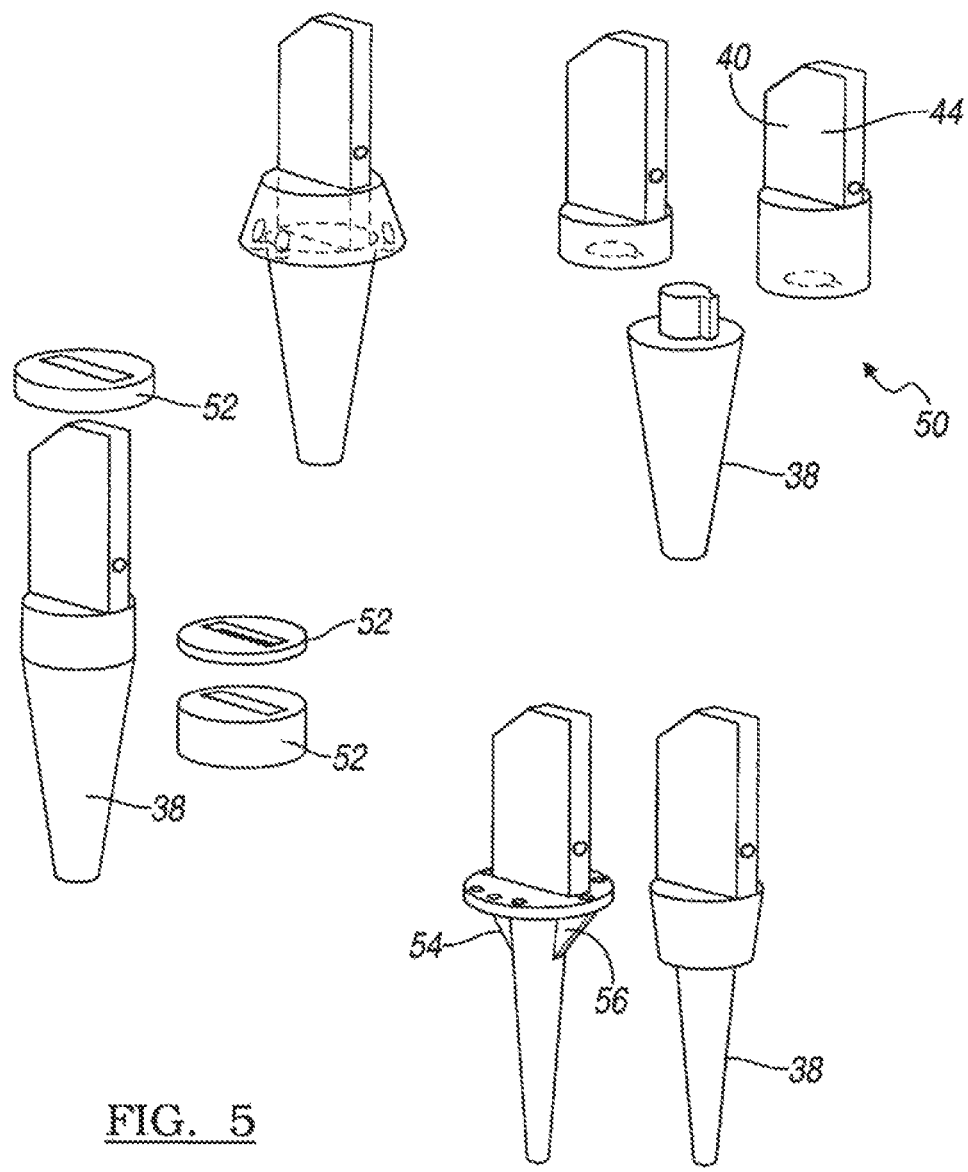
FIG. 5 represents a kit of stems according to present teachings.

FIG. 5 details the mechanism for coupling an eccentric modular ulnar head on the implanted stem. The stem may include either fixed or modular components 50 that allow for varying the length, outside peripheral configuration and distal support sleeves 52 so as to accommodate a wide range of clinical circumstances. In particular, the modular sleeves 52 may be configured to be positioned proximate to the distal aspect of the stem and have various heights and outside tapered or cylindrical configurations. Alternatively, the ulnar stem may be fabricated as a monolithic structure with the sleeve configuration being integral to the stem. The ulnar stem may also include an anti-rotation member 54 that may be configured as a longitudinally running flair 56, flange or fin. It is well known in the art that other configured structures extending from the shaft of the stem that inhibit rotation of the device post-implantation in the medullary canal are contemplated herein, including but not limited to surface treatments, a plurality of structures that ring the circumference of the stem, etc.

FIGS. 6A-6E represent an alternate ulnar prosthetic according to the present teachings. The prosthetic is formed of a body 62 having a coupling stem 64. Disposed on a distal end of the body 62 can be a T-shaped coupling flange configured to engage a congruent slot formed within the head portion. The slot is formed on a generally planar surface 63 formed on a planar proximal surface defined within the head. It is envisioned the pair of planar sides can be perpendicular to each other. Further, one planar surface may be parallel to an axis defined by the coupling stem. The body 62 can be coupled to a stem using a coupling taper.

Figure 6A:
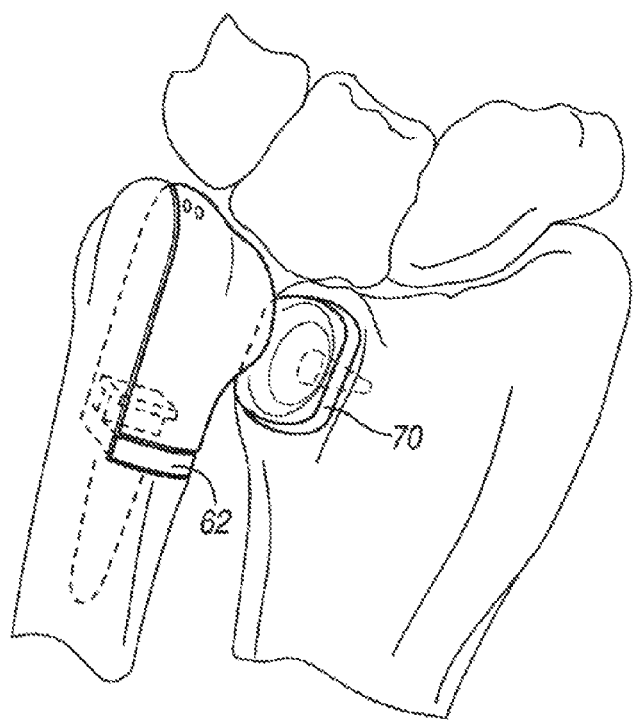
FIGS. 6A-6E represent perspective and cross-sectional views of the prosthetic according to the present teachings.
Figure 6C:
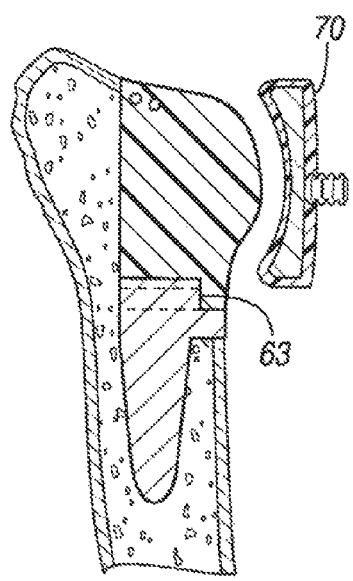
Figure 6B:
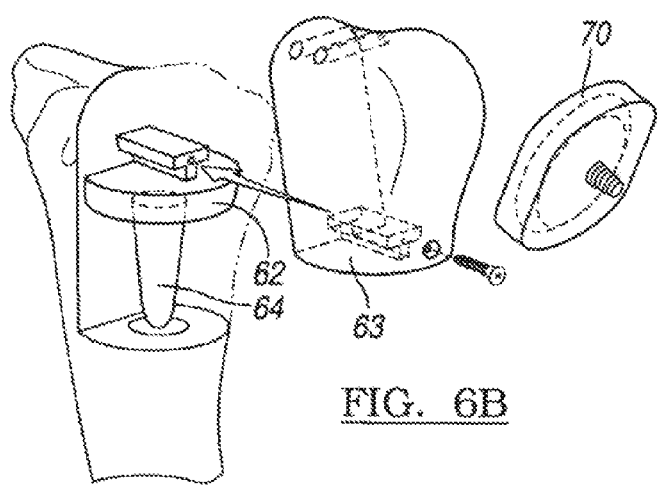
Figure 6D:
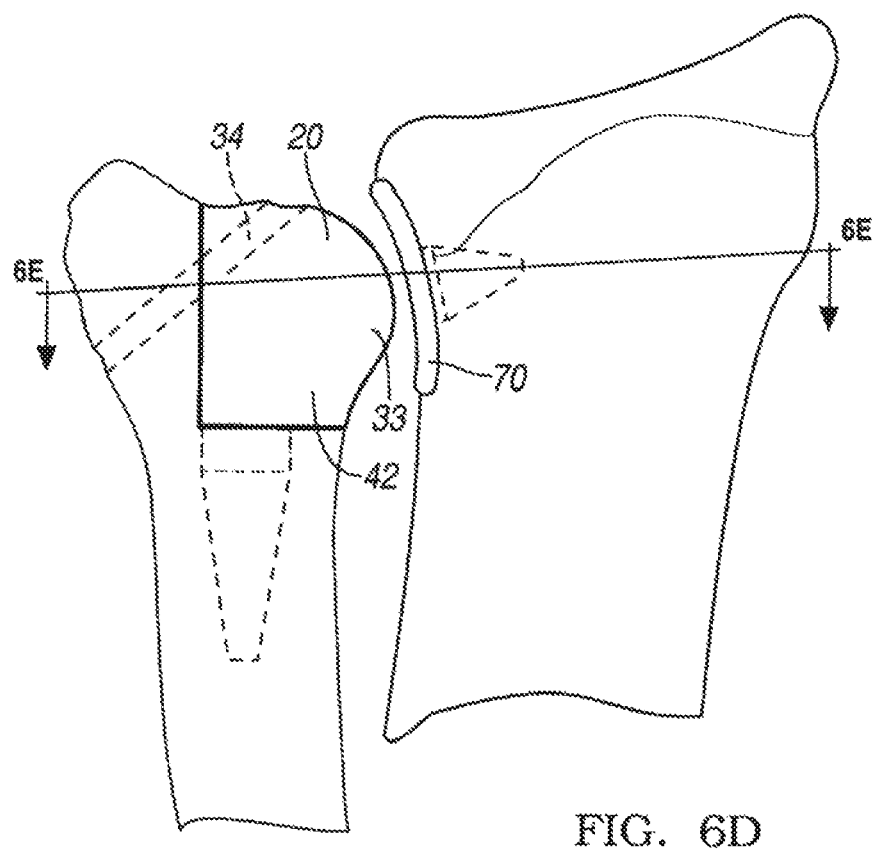
Figure 6E:
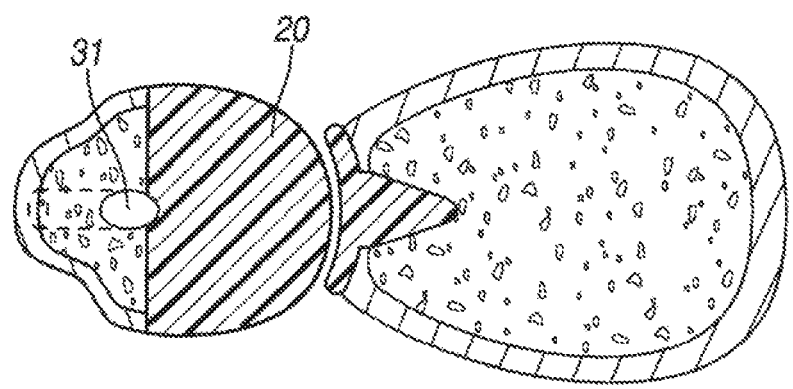
Figure 7A:
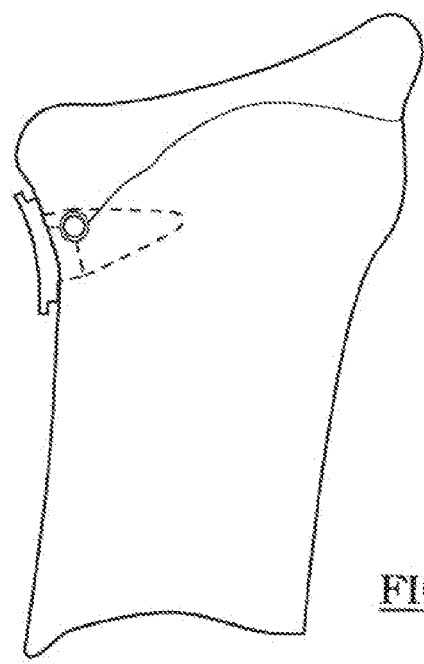
FIGS. 7A-7F represent top and side views of the alternate teachings according to the present disclosure.
Figure 7B:
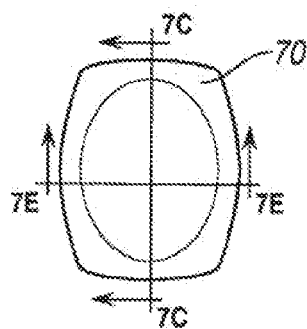
Figure 7C:
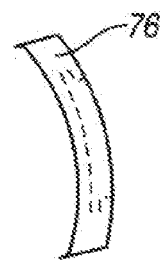
Figure 7D:
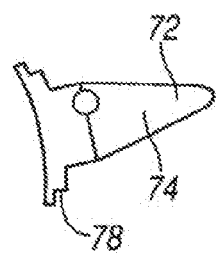
Figure 7E:
Figure 7F:
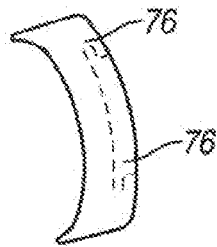

As best seen in FIG. 6B, the medial side of the head is generally planar, and is configured to bear against a corresponding flat planar surface defined in the resected ulna. Further shown is a second prosthetic implanted into the radius. The second prosthetic 70 is configured to place an articulating surface at the radial sigmoidal notch. The second prosthetic can be monolithic and formed of a polymer or PEEK material.

As seen in FIGS. 7A-7F, the second prosthetic 70 can be formed of a base member 72 having a fixation stem 74 and a modular polymer bearing surface 76. The base member 72 can have a stepped coupling region 78 configured to couple with a corresponding locking feature defined within the polymer bearing surface 76. It should be noted the base member 72 can be integrally molded into the polymer 76, exposing the stem portion 74 therefrom.

Figure 8A:
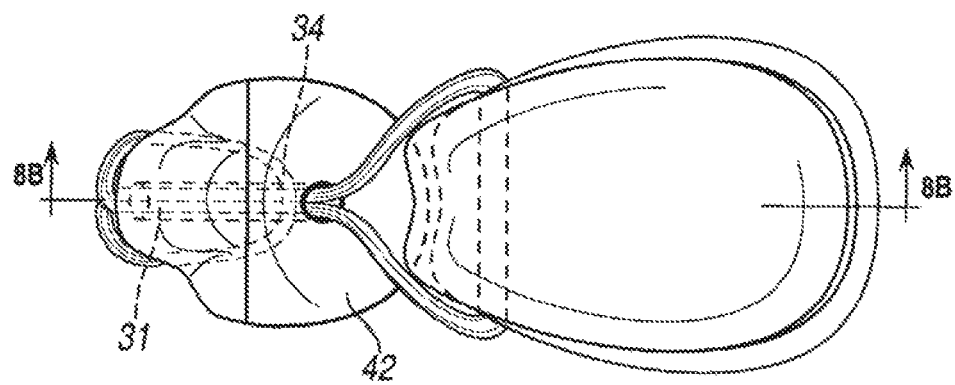
FIGS. 8A-9 represent views of an alternate prosthetic system according to the present teachings.
Figure 8B:
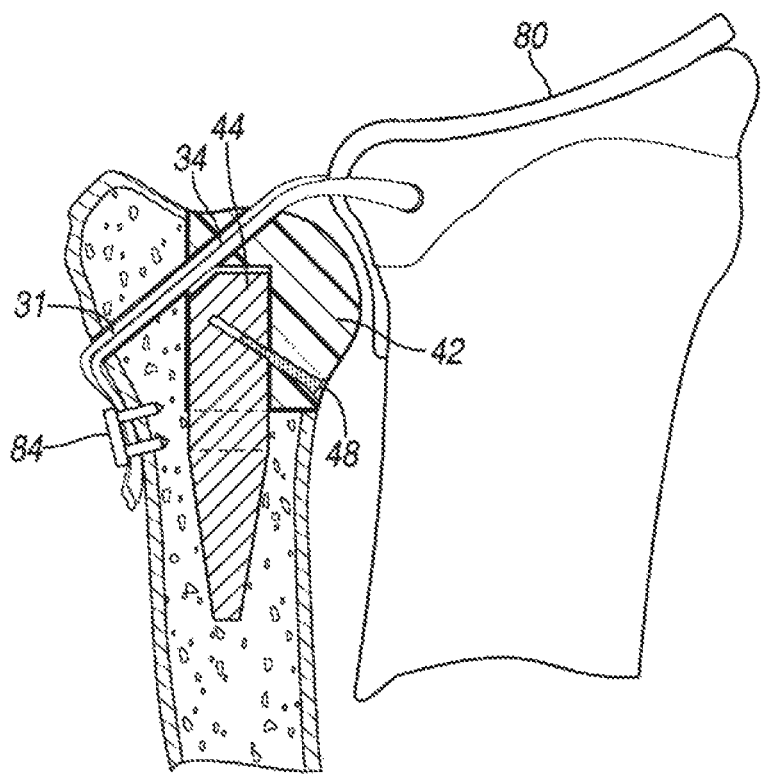
Figure 8C:
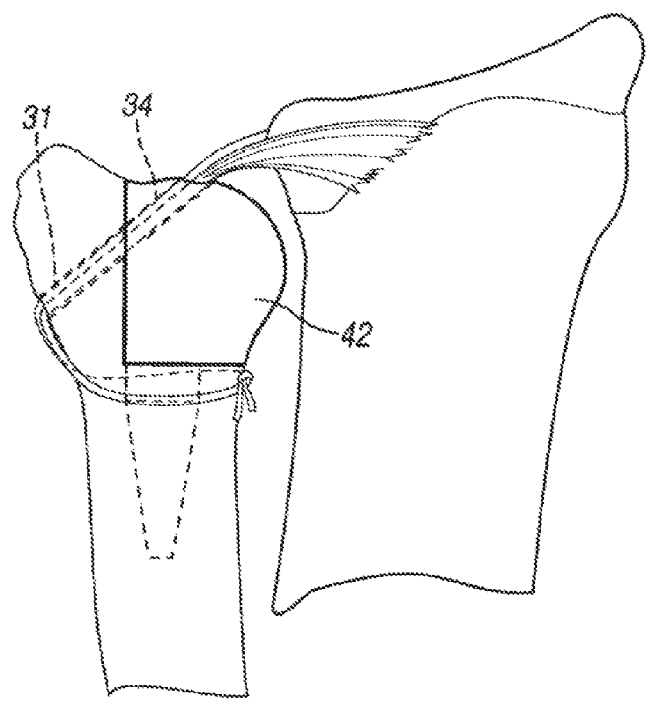

FIGS. 8A and 8B represent an alternate example of the mechanism that may be used for soft tissue stabilization of the distal radioulnar joint post-implantation of the invention. As shown, the soft tissue structure or coupling suture may be passed through a hole, slot or other like portal that is located in the medial portion of the radial implant or sigmoid notch device of the system and connect with either the ulnar component or the remaining bone stock of the distal ulna.

Optionally, the radius can have a modular resurfacing prosthetic 80. The resurfacing prosthetic can have both distal and medial bearing surfaces. The soft tissue can be tied or fastened to the ulna using a soft tissue coupling fastener 84.

Figure 9:
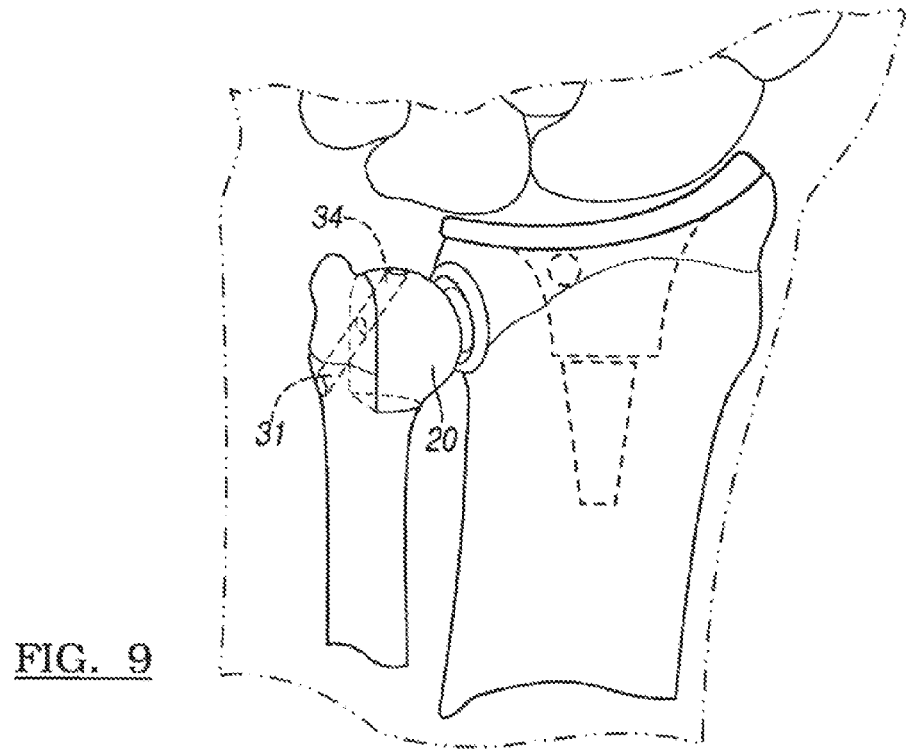
Figure 10A:
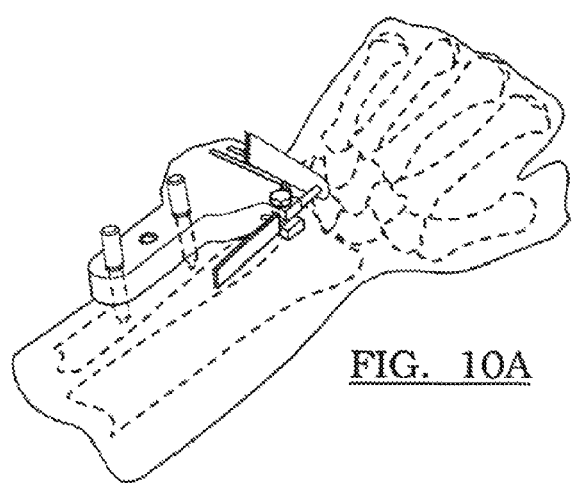
FIGS. 10A-10D represent tools configured to be used to implant the prosthetics shown in FIGS. 1-8.
Figure 10B:
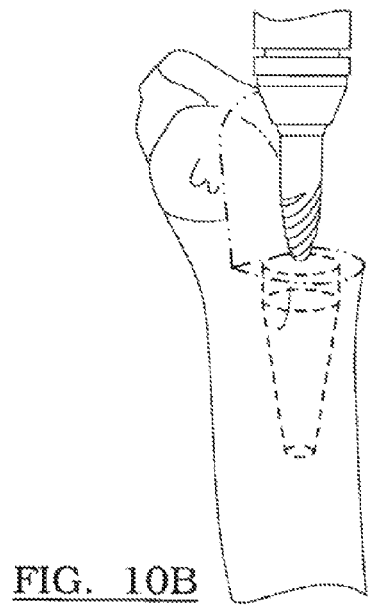
Figure 10C:
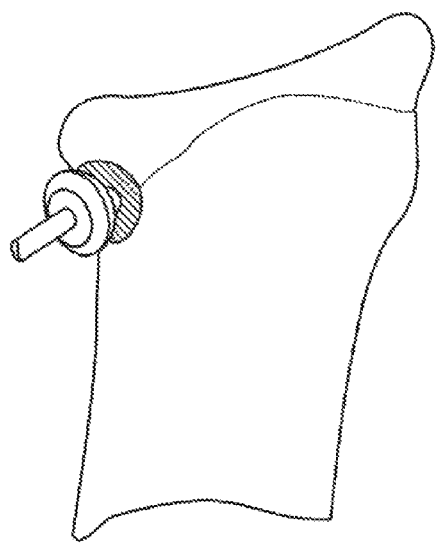
Figure 10D:
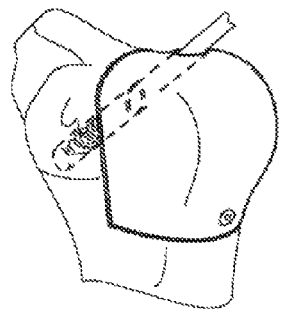

FIG. 9 depicts a prosthetic which can be configured in a variety of cross-sectional shapes, including but not limited to circular, oval, and eccentric or biased in some manner. Also depicted in FIGS. 10A through 10D are the various instruments that will be used for implanting the invention. These include various cutting jigs for resecting the bony structures including, the ulnar head and the sigmoid notch. Also disclosed are various sized canal reamers and resection guides for preparing the distal aspect of the ulna.

Attachments 11A-11C depict another aspect of the teachings with the ulnar implant being positioned to articulate with a sigmoid notch resurfacing implant. As described, the sigmoid notch device may be fabricated as one piece poly component that includes a uniquely shaped articulating surface that allows for full range of motion, but also will constrain the ulnar head so as to minimize the possibility of dislocation post-operatively. The concavity of the articulating surface may be configured to provide various degrees of stability depending on the presented clinical situation and the integrity of the surrounding soft tissue. The sigmoid notch device 70 may also be constructed using a metal backing or support and a plastic articulation surface component that are connected or coupled in some fashion. The sigmoid notch device 70 may include a hole, portal or other attachment mechanism that allows for soft tissue connection. An integral attachment mechanism may be located in the sigmoid notch implant and may require a corresponding opening be prepared through the surrounding bone. Having this sort of hybrid arrangement may further facilitate attachment strength and joint stabilization. An alternative configuration of the sigmoid notch device 70 may include the soft-tissue attachment site being positioned post-implantation, either flush or superior to the bone surface to facilitate tensing of the soft-tissue.

Figure 11A:
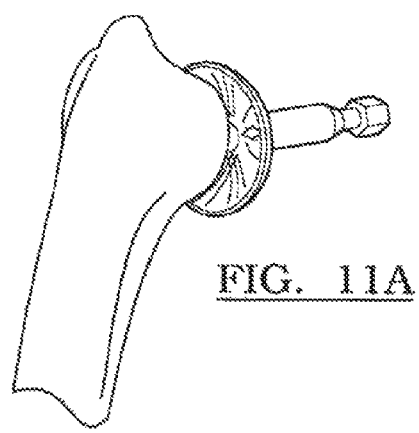
FIGS. 11A-11C represent first, side, and cross-sectional views of a distal ulna prosthetic according to the present teachings.
Figure 11B:
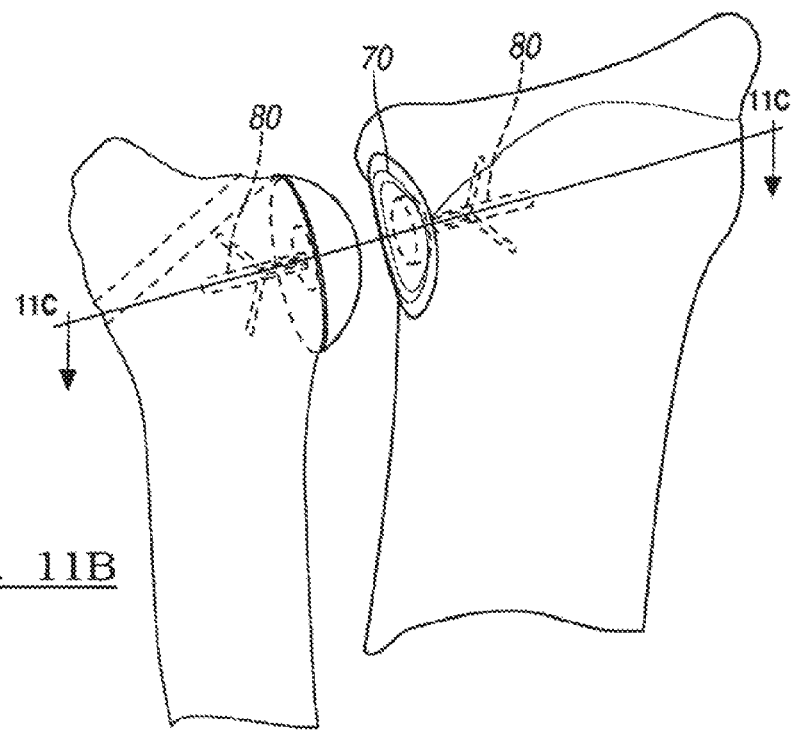
Figure 11C:
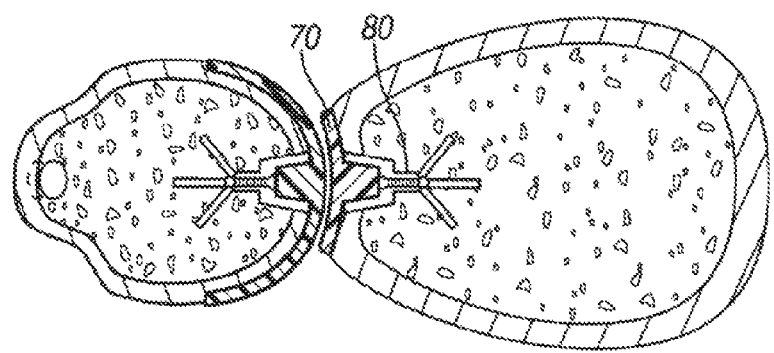

As best seen in FIGS. 11B-11C, the sigmoid notch resurfacing device may also have a central fin or keel like structure that extends from the undersurface of the polyarticulating surface (for the all-poly embodiment) and from the undersurface of the metal portion for the metal backed version. The central fin/keel 80 functions to resist rotation and translational forces during the range of motion cycle of the joint post-operatively. Other centralized fixation structures are contemplated, including but not limited to, singular or a plurality of pins, posts or other extension-like structures.

The sigmoid notch resurfacing device 70 can include deployable legs or projections that extend from the central anti-rotation structure. As shown, the device 70 includes a mechanism that when turned would result in the legs/projections contacting and integrating with the surrounding cancellous bone as they extend from the centralized fin/keel 80. The implantation process may include placing the device in final position within the notch and then turning a screw or other like mechanism that would result in the legs moving away from the fin/keel 80 and fixating within the surrounding bone.

The resurfacing implant 82 is positioned on the medial aspect of the ulnar head 84 following decortication of the existing bone or an alternative bony preparation process. The implant 82 includes an articulation portion 86 that has a convex shape and functions to replicate the existing articulating surface of the ulnar head 84. The purpose of such a resurfacing implant is to minimize the removal of host bone while reproducing the natural articulating surface of the ulnar head 84. The ulnar head resurfacing implant may be fixed to the remaining bone stock by a central keel or fin projection that extends from the undersurface of the implant. Other modes of fixation may also be used, like screws, pins, spikes, etc. The implant may be fabricated as an all-poly or all-metal component to minimize implant thickness, or alternatively as a metal back device with a slightly convex poly or other polymer component that functions as the articulating surface. As discussed above, the ulnar head resurfacing implant may also use legs that are deployable from the central keel. The mechanism of operation of these legs is the same as described for the sigmoid notch implant above.

Figure 12A:
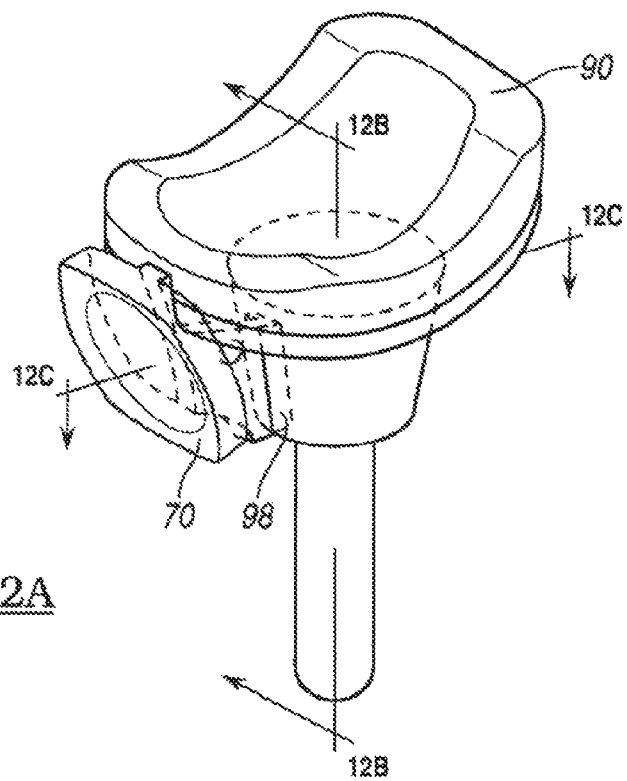
FIGS. 12A-12C represent perspective and cross-sectional views of the prosthetic according to the present teachings.
Figure 12B:
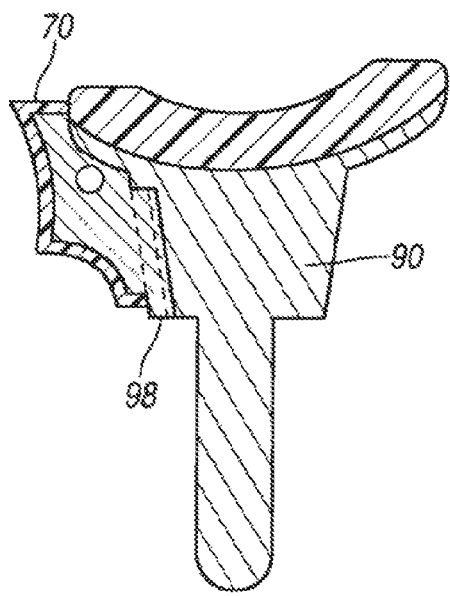
Figure 12C:
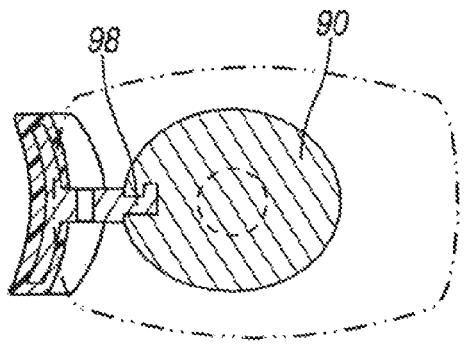

As shown in FIGS. 12A-12C, included is a radial component 90 that articulates with an existing commercially available device. The distal radial component 90 includes a body that includes a stem, a medial connection on a medial side of the body, and a distal articulating surface. Included is a sigmoid notch portion 94 that is securely attached to the radial implant so as to allow for unrestricted articulation with the ulnar device. As shown, the medial connection such as a fin or other sliding mechanism 96 may be used to attach the sigmoid notch implant to the existing radial component 90.

The surgical procedure for implanting the radial head surface replacement device and sigmoid notch resurfacing implant may include the steps of making a small dorsal incision in the wrist. The next step may be to make a resection in portion of the sigmoid notch that is of adequate size to allow for the insertion of the sigmoid notch device. Following the preparation of the sigmoid notch, the forearm will be pronated and supinated allowing the surgeon to decorticate the ulnar head so that the resurfacing implant may be inserted. Following the insertion of the resurfacing head, the surgeon may take the next step of implanting the sigmoid notch device, taking special care to properly align the central keel/fin. Depending on what embodiment of the sigmoid notch device is used, the surgeon may need to take the further step of deploying the cancellous legs within the sigmoid notch device central keel to achieve adequate fixation within the bone. The next step may include maneuvering the implanted device system through a range of motion and then, closing the wound in a generally accepted manner.

The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps may be employed.

When an element or layer is referred to as being "on," "engaged to," "connected to," or "coupled to" another element or layer, it may be directly on, engaged, connected or coupled to the other element or layer, or intervening elements or layers may be present. In contrast, when an element is referred to as being "directly on," "directly engaged to," "directly connected to," or "directly coupled to" another element or layer, there may be no intervening elements or layers present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. may be used herein to describe various elements, components, regions, layers and/or sections, these elements, components, regions, layers and/or sections should not be limited by these terms. These terms may be only used to distinguish one element, component, region, layer or section from another region, layer or section. Terms such as "first," "second," and other numerical terms when used herein do not imply a sequence or order unless clearly indicated by the context. Thus, a first element, component, region, layer or section discussed below could be termed a second element, component, region, layer or section without departing from the teachings of the example embodiments.

Spatially relative terms, such as "inner," "outer," "beneath," "below," "lower," "above," "upper," and the like, may be used herein for ease of description to describe one element or feature's relationship to another element(s) or feature(s) as illustrated in the figures. Spatially relative terms may be intended to encompass different orientations of the device in use or operation in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptors used herein interpreted accordingly.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method of implanting a distal wrist implant relative to a host radius, the method comprising:
    selecting a distal radial component, the radial component having a body that includes a stem, a medial connection on a medial side of the body, and a distal articulating surface, the distal articulating surface extending over and beyond the medial connection in a medial direction;
    implanting the distal radial component relative to the host radius; and
    securing a sigmoidal notch prosthetic, which is separate from the distal radial component including the distal articulating surface of the distal radial component, to the radial component at the medial connection using a sliding mechanism operable between the sigmoidal notch prosthetic and the distal radial component in a direction along the medial connection towards the distal articulating surface, wherein the sigmoidal notch prosthetic includes a bearing surface exposed in a direction away from the medial side of the distal radial component.

2. The method of claim 1, further comprising coupling a flexible member to the sigmoidal notch prosthetic.

3. The method of claim 2, wherein coupling the flexible member comprises locating the flexible member through an aperture formed in the sigmoidal notch prosthetic.

4. The method of claim 3, wherein locating the flexible member comprises passing one of a suture or wire through the aperture.

5. The method of claim 4, wherein the medial connection is located between the stem and the distal articulating surface.

6. The method of claim 1, wherein the medial connection is located between the articulating surface of the distal radial component and the host radius.

7. A method of implanting a distal radial wrist implant, the method comprising:
    implanting a distal radial component relative to a host radius using a stem of the distal radial component, the distal radial component including a distal articulating surface;
    securing at least a portion of the distal radial component to the host radius; and
    coupling a sigmoidal notch prosthetic, which is separate from the distal radial component including the distal articulating surface of the distal radial component, to a medial side of the distal radial component using a sliding mechanism operable between the sigmoidal notch prosthetic and a medial connection on the medial side of the distal radial component in a direction along the medial connection towards the distal articulating surface, wherein the distal articulating surface extends over and beyond the medial connection in a medial direction, and wherein the sigmoidal notch prosthetic includes a bearing surface exposed in a direction away from the medial side of the distal radial component.

8. The method of claim 7, further comprises locating a flexible member around at least a portion of the sigmoidal notch prosthetic.

9. The method of claim 8, wherein locating the flexible member comprises locating the flexible member through an aperture defined in the sigmoidal notch prosthetic.

10. The method of claim 9, wherein locating the flexible member comprises passing one of a suture or wire through the aperture.

11. The method of claim 10, comprising locating the sigmoidal notch prosthetic adjacent to the host radius.

\* \* \* \* \*